United States Patent [19]

Ohnesorge et al.

[11] Patent Number: 5,666,391

[45] Date of Patent: Sep. 9, 1997

[54] X-RAY EXAMINATION SYSTEM WITH IDENTIFICATION OF AND COMPENSATION FOR SUBJECT-PRODUCED SCATTERED RADIATION TO REDUCE IMAGE ARTIFACTS

[75] Inventors: Bernd Ohnesorge; Ernstpeter Ruehrnschopf, both of Erlangen; Klaus Klingenbeck-Regn, Nuremberg, all of Germany

[73] Assignee: Siemens Aktiengesellschaft, Munich, Germany

[21] Appl. No.: 669,931

[22] Filed: Jun. 25, 1996

[30] Foreign Application Priority Data

Jun. 26, 1995 [DE] Germany ............. 195 23 090.6

[51] Int. Cl.$^6$ ..................... H05G 1/60
[52] U.S. Cl. .............. 378/7; 378/98.11; 378/98.12
[58] Field of Search .................. 378/7, 19, 98.11, 378/98.12, 98.4, 901; 364/413.17, 413.18, 413.19, 413.2, 413.21, 413.14, 413.16, 413.23, 413.13

[56] References Cited

U.S. PATENT DOCUMENTS

| | | |
|---|---|---|
| 4,114,041 | 9/1978 | Oliver. |
| 4,203,036 | 5/1980 | Tschunt. |
| 4,812,983 | 3/1989 | Gullberg et al. ............ 378/901 |

FOREIGN PATENT DOCUMENTS 2 021 896  12/1979  United Kingdom.

*Primary Examiner*—Don Wong
*Attorney, Agent, or Firm*—Hill, Steadman & Simpson

[57] ABSTRACT

An x-ray examination apparatus with a detector array having a number of detector elements includes a data correction computer in which the subject-scattered radiation can be numerically determined and corrected. The forward scatter intensity is determined by multiplication of the measured intensities, windowed with a window function, with the natural logarithm of the intensity normalized with the unattenuated primary intensity. The subject-scattered radiation can then be calculated and corrected through filtering of the forward scatter intensity with a convolution kernel and a suitable scaling.

12 Claims, 2 Drawing Sheets

X-RAY EXAMINATION SYSTEM WITH IDENTIFICATION OF AND COMPENSATION FOR SUBJECT-PRODUCED SCATTERED RADIATION TO REDUCE IMAGE ARTIFACTS

BACKGROUND OF THE INVENTION

1. Field of the Invention

The present invention is directed to an x-ray examination system of the type wherein scattered radiation produced by the examination subject can result in image artifacts.

2. Description of the Prior Art

In x-ray examination equipment, e.g. an x-ray computed tomography system, subject-scattered radiation can occur that can lead to image artifacts, which can make diagnosis by a physician more difficult. In order to reduce the effect of scattered radiation, it is possible, e.g. in third-generation x-ray computed tomography system with a rotating tube detector measurement arrangement, to provide collimator plates between the detector elements that are oriented toward the tube focus so as to provide partial shielding against the obliquely incident scattered radiation. Such collimator plates have only limited utility in fourth-generation x-ray computed tomography systems, which have a fixed detector ring and a rotating x-ray tube, since they screen out not only scattered radiation but also parts of the measurement radiation. In fourth-generation x-ray computed tomography systems, the portion of scattered radiation in the measurement data is considerable, and a subsequent correction for the presence of the scattered radiation is unavoidable for a good image quality. In third-generation x-ray computed tomography systems, the corruption of data through scattered radiation is lower, but can still lead to disturbing artifacts. A correction is thus advisable in third-generation systems as well.

SUMMARY OF THE INVENTION

An object of the present invention is to provide an x-ray examination apparatus wherein an efficient computer determination of the intensity of the scattered radiation ensues, on the basis of which a correction of the measurement data can be carried out.

The above object is achieved in accordance with the principles of the present invention in an x-ray examination apparatus having a detector array composed of a number of detector elements, each detector element generating an output signal representative of the intensity distribution of all x-rays (primary as well as scattered) incident thereon, wherein a forward scatter intensity is determined, for each output signal, by multiplying the measured intensities, windowed with a window function, with the natural logarithm of the intensity distribution.

In determining the forward scatter intensity, the intensity distribution can be normalized with respect to the primary radiation intensity (i.e., the intensity of the radiation upon its emission from the x-ray source) before taking the natural logarithm, i.e., the natural logarithm of the intensity distribution divided by the unattenuated primary intensity is taken.

The generation of the scatter radiation can be considered as if a source of scatter radiation is contained at a location within the examination subject, in which case the scatter intensity reaching a given detector element will be dependent on the distance of this scatter intensity source from the x-ray source and the detector element. In order to obtain a contribution to the total scatter determination from all such scatter sources in the examination subject, a distance function can be identified, which identifies the contribution of an x-ray to the overall scatter intensity distribution detected by a given detector element which is made by each scatter source being struck by the x-ray dependent on its distance from the detector element. The contribution of the total scatter intensity can then be identified by a convolution of the forward scatter intensity distribution, identified as described above, with the distance function.

The total scatter intensity determined in this manner for each output signal is then subtracted from that output signal, to obtain output signal. The calculation (construction) of the x-ray image then takes place using any suitable known image construction technique, but using the corrected output signals (corrected image intensities) instead of the "raw" or uncorrected output signals.

Other factors can also be taken into account by multiplying these factors with the result obtained as described above. For example, a weighting can be undertaken by multiplication with a function which is dependent on the distance of the center of gravity of the scatter body to the detector array. A scale constant can also be multiplied, the scale constant being obtained, for example, from a table which identifies different constants for a particular examination subject dependent on the scan layer thickness.

In order to reduce the computing expense (computing time), samples of the measured data can be taken in all dimensions before conducting the aforementioned convolution, with subsequent interpolation of the convolution result.

The invention is suited in general for use in x-ray computed tomography systems, but can also be used with other x-ray examination equipment wherein digital data processing takes place.

DESCRIPTION OF THE PREFERRED EMBODIMENTS

Figure 1:
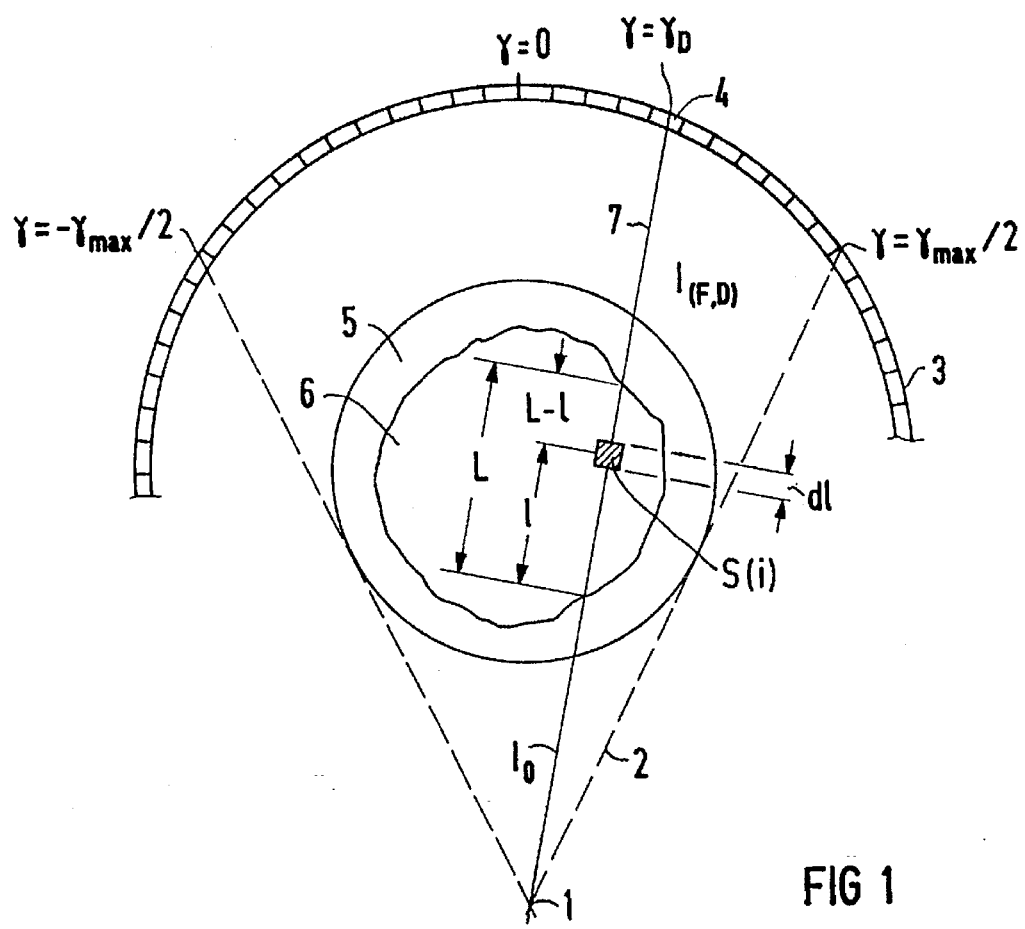
FIG. 1 shows the basic parts of a fourth-generation x-ray computed tomography apparatus, for an explanation of the basic concept of the invention.

In the computed tomography apparatus shown in FIG. 1, the focus 1 of an x-ray tube is shown, from which a fan-shaped x-ray beam 2 is emitted, which strikes a detector array 3 of annular construction. A detector element of the detector array 3 is designated with 4. The x-ray beam 2 penetrates a subject 6 arranged in a measurement field 5 preceding the detection 3.

The basic idea of the filtering correction of the invention is to obtain the distribution of the overall scatter intensity within a projection by means of a weighting of the intensity values of this projection and subsequent convolution with a kernel. The values for the weighting and the convolution kernel follow from a physical model based on what is known as the forward scatter.

The measurement ray 7 of the x-ray beam 2 is analyzed for explaining the invention. The ray 7 emanates from the focus 1 and terminates at the represented position in the detector element 4. As indicated in FIG. 1, after traversing a path l in the subject 6, the ray 7 reaches the scatter center S(i), having a longitudinal extension dl in the direction of radiation. A part of the scatter intensity (the forward scatter) emanating from S(i) is radiated at such small angles that it reaches the detector element 4 as the intensity $I_{(F,D)}$ of the weakened measurement ray 7 of the detector element 4. It is assumed that the forward scatter intensity $dI_{sc}^{(0)}$ forw, s(i), (F,D), which is present directly behind the scatter center S(i), depends on the electron density of the scatter center S(i) and thus on the attenuation value $\mu_{S(i)}$, the extension and the intensity of the measurement beam 7 arriving at S(i). With the proportionality constant $K_{sc,forw}$ and the unattenuated primary intensity $I_0$, $$dI^{(0)}_{sc,forw,S(i),F,D)} = K_{sc,forw}\mu_{S(i)}I_0 \exp\left(-\int_0^l \mu(\lambda)d\lambda\right) dl \quad (1)$$

is valid. As shown in (1) above, the term "exponentiating" as used herein means the base e (natural) exponentiation function.

Before the forward-scattered quanta reach the detector 3, they still have to traverse approximately the path L-l up to the exit point of the measurement ray 7 from the subject 6. Only new scatter processes producing scattered photons leaving the detection plane are assumed to appear. A part of the forward-scattered quanta are absorbed. After the multiplication of equality (1) with the exponential term of the corresponding line integral via the attenuation value, the following results for the forward scatter intensity $dI_{sc,forw,S(i),(F,D)}$ which emanates from the scatter center S(i) and is registered in the detector element 4, $$dI_{sc,forw,S(i),(F,D)} = \quad (2)$$

$$K_{sc,forw}\mu_{S(i)}I_0 \exp\left(-\int_0^l \lambda d\lambda\right) \exp\left(-\int_l^L \mu(\lambda)d\lambda\right) dl,$$

which yields, $$dI_{sc,forw,S(i),(F,D)} = K_{sc,forw}\mu_{S(i)}I_0 \exp\left(-\int_0^l \lambda d\lambda\right) dl$$

If now a continuous scatter center distribution in the subject 6 along the measurement ray 7 is assumed, the total forward scatter intensity $I_{sc,forw,(F,D)}$ in the detector 3 is obtained by integration of the attenuation values $\mu_{S(i)}$, present at the locus of the scatter centers, over the entire path of the measurement beam 7 in the subject 6:

$$I_{sc,forw,(F,D)} = K_{sc,forw}I_0 \exp\left(-\int_0^L \mu(\lambda)d\lambda\right) \int_0^L \mu_{S(i)}(l)dl \quad (3)$$

The product of the unattenuated primary intensity $I_0$ and the exponential term of the line integral is equal to the attenuated intensity $I_{(F,D)}$ of the measurement ray 7 after its exiting from the subject 6. The line integral can be correspondingly formulated with the natural logarithm of the quotient $I_{(F,D)}/I_0$:

$$I_{sc,forw,(F,D)} = K_{sc,forw}I_{(F,D)}(-\ln I_{(F,D)}/I_0) \quad (4)$$

According to FIG. 1, given a central angle $\gamma_D$, the detector lies within the focus fan at the focus position F. On the basis of $I_{sc,forw,(F,D)}$, the scatter intensities supplied by the measurement beam in all detector elements of the x-ray beam 2 with $\gamma \in [-\gamma_{max}/2; \gamma_{max}/2]$ can be empirically determined.

Figure 2:
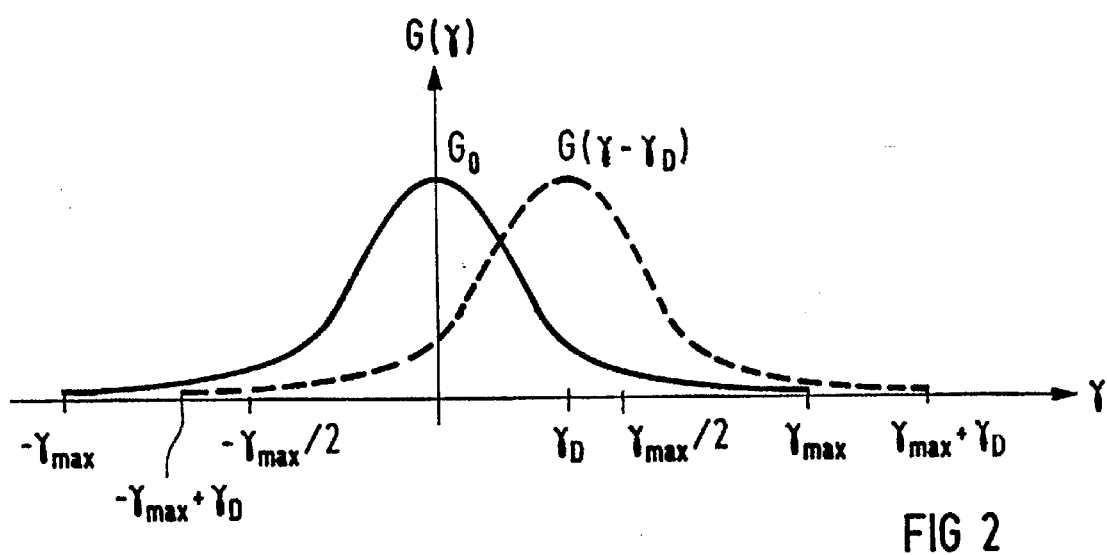
FIGS. 2 and 3 show curves for the explanation of the invention in conjunction with FIG. 1.

The principal scatter element dependencies of the differential effective cross-sections and scatter energies of Compton and Rayleigh scattering for scatter angles $\Psi \in [-\pi/2; \pi/2]$ in axially symmetric scatter processes justify the assumption that the scatter contributions to a detector element from the measurement ray 7 follow a certain dependence of the distance of the detector element to the detector element 4. A distance function, $G(\gamma-\gamma_D)$, that can be used for description and is qualitatively shown in FIG. 2, covers the angle area $[-\gamma_{max}+\gamma_D; \gamma_{max}+\gamma_D]$. If the relevant detector element lies with $\gamma_D = \pm \gamma_{max}/2$ at one edge of the x-ray beam 2, the distance function then also reaches the detector elements at the other edge.

The foregoing considerations show that the measurement ray 7 in the detector element 4 causes the forward scatter intensity $I_{sc,forw,(F,D)}$. It is now assumed that the scatter contributions $I_{sc,(F,D)}(\gamma)$ in the other detector elements in the x-ray beam 2, given the central angles $\gamma \in [-\gamma_{max}/2; \gamma_{max}/2]$, result from the product of the forward scatter intensity and the distance function.

$$I_{sc,forw,(F,D)}(\gamma) = I_{sc,forw,(F,D)}G(\gamma-\gamma_D)R(\gamma) \quad (5)$$

with $$R(\gamma) = \begin{cases} 1; & \gamma \in [-\gamma_{max}/2; \gamma_{max}/2] \\ 0; & \text{otherwise} \end{cases}$$

In order to calculate the distribution of the overall scatter intensity $I_{sc}(\gamma)$ in the x-ray beam 2 at the focus position, the contributions of all the rays in the fan at all the detector elements must be summed. Assuming a continuous detector distribution and continuous fan radiation, an integration of (5) over all possible detector positions with the central angle $\gamma_D$ is additionally necessary:

$$I_{sc}(\gamma) = \int_{-\gamma_{max}/2}^{\gamma_{max}/2} I_{sc,forw}(\gamma_D)G(\gamma-\gamma_D)d\gamma_D R(\gamma) \quad (6)$$

$I_{sc,forw}(\gamma_D)$ is here the forward scatter intensity in a detector element with the central angle $\gamma_D$ in the focus fan. The integral in (6) represents a convolution of the distribution of the forward scatter intensities in the focus fan with the distance function $G(\gamma)$:

$$I_{sc}(\gamma) = [I_{sc,forw}(\gamma)*G(\gamma)]R(\gamma) \quad (7)$$

From (4), neglecting the scatter energy portion in the measured data, the distribution of the forward scatter intensities can be approximately determined with (8) from the measured projection data $I_{dist}(\gamma)$ of the focus fan.

$$I_{sc,forw}(\gamma) \approx K_{sc,forw}I_{dist}(\gamma)\left(-\ln \frac{I_{dist}(\gamma)}{I_0}\right) \quad (8)$$

actual correction consists in the subtraction of the determined scatter intensities from the intensity values of the measured data. The approximation (8) makes clear that this method does not require a reference image, but rather makes use exclusively of the measured projection data. An efficient algorithm, however, requires extensive investigation of the form of the distance function and the size of the proportionality constant $K_{sc,forw}$, so that the physical conditions can be reproduced as well as possible with this model.

The correction equation (9), from which the scatter intensities in the channels of all the detector fans are determined from the measured intensity values $I_{dist}(\delta, \gamma)$, contains, besides the convolution of the forward scatter distribution with the distance function, another weighting, $f(\Delta z_{st})$, that depends on the layer thickness. In addition to this, there is a projection-dependent weighting $g(a(\delta))$ for the particular treatment of eccentric subjects and a scaling with the machine constant $C_M$.

$$I_{sc}(\delta,\gamma) = C_M f(\Delta z_{sl}) g(a(\delta)) [I_{sc,forw}(\delta,\gamma) * G(\gamma)] R(\gamma)$$

with $$I_{sc,forw}(\delta,\gamma) = K_{sc,forw}[W_\epsilon\{I_{dist}(\delta,\gamma)\}]^p \left[ -\ln \frac{I_{dist}(\delta,\gamma)}{I_0} \right]^q$$

wherein $$W_\epsilon\{I_{dist}(\delta,\gamma)\} = \begin{cases} I_{dist}(\delta,\gamma); & I_{dist}(\delta,\gamma) < \epsilon I_0 \\ 0; & \text{otherwise} \end{cases} \quad (9)$$

$(\delta,\gamma)$ are the continuous central angle coordinates of the focus position and the channels in the focus fan projections $R(\gamma)$ is obtained from (7).

In the calculation of the forward scatter intensity, a windowing $W_\epsilon\{.\}$ with $0<\epsilon<1$ is also included, which sets a suitable limit for the intensity values to be used. On the basis of empirical investigations, the use of the windowed intensity and of the line integral to the power of the real numbers, with the parameters p and q proves to be advisable.

As the distance function G, e.g., the function shown at (10) can be used, with the adaptation of the formal parameter A. Every other function of the central detector angle $\gamma$, with the character in principle from FIG. 2 or another shape, is also conceivable. The distance function describes the form of the scatter distribution caused in the detectors by a single measurement ray. The distance function G can easily be determined by means of simulation or measurement of the scatter for what is known as a "pencil" beam in the observed apparatus geometry.

$$G(\gamma) = \frac{G_0}{1 + \left(\frac{\gamma}{A}\right)^2} \; ; \; \gamma \in [-\gamma_{max}, \gamma_{max}] \quad (10)$$

The shape of the distance function can be varied with the extension of the subject perpendicular to the direction of projection and the tissue density of the object in direction of projection estimated from the measured data. For eccentric subjects, the weighting function g(a) of the distance a of the scatter body center of gravity to the detector 3 is taken into account. The value a is projection-dependent, and thus changes with $\delta$. $K_{0,a}$, $K_{1,a}$ and r are constants to be determined empirically and the tissue density of the object in the direction of projection is estimated from the measured data.

$$g(a(\delta)) = K_{0,a} + K_{1,a} \left( \frac{1}{a(\delta)} \right)^r \quad (11)$$

$K_{sc,forw}$ proves to be subject-dependent. For example, the minimum intensity value in the measured data set or the maximum extension of the subject can be chosen as the parameters characterizing the subject. Tables can be used for various layer thicknesses for the quantities $K_{sc}$ defined in (12). In (12), the subject is described through the minimum intensity in the data set that is normalized to the unattenuated primary intensity.

$$K_{sc}(\Delta z_{S1}, I_{min}/I_0) = C_M f(\Delta z_{S1}) G_0 K_{sc,forw}(I_{min}/I_0) \quad (12)$$

Figure 3:
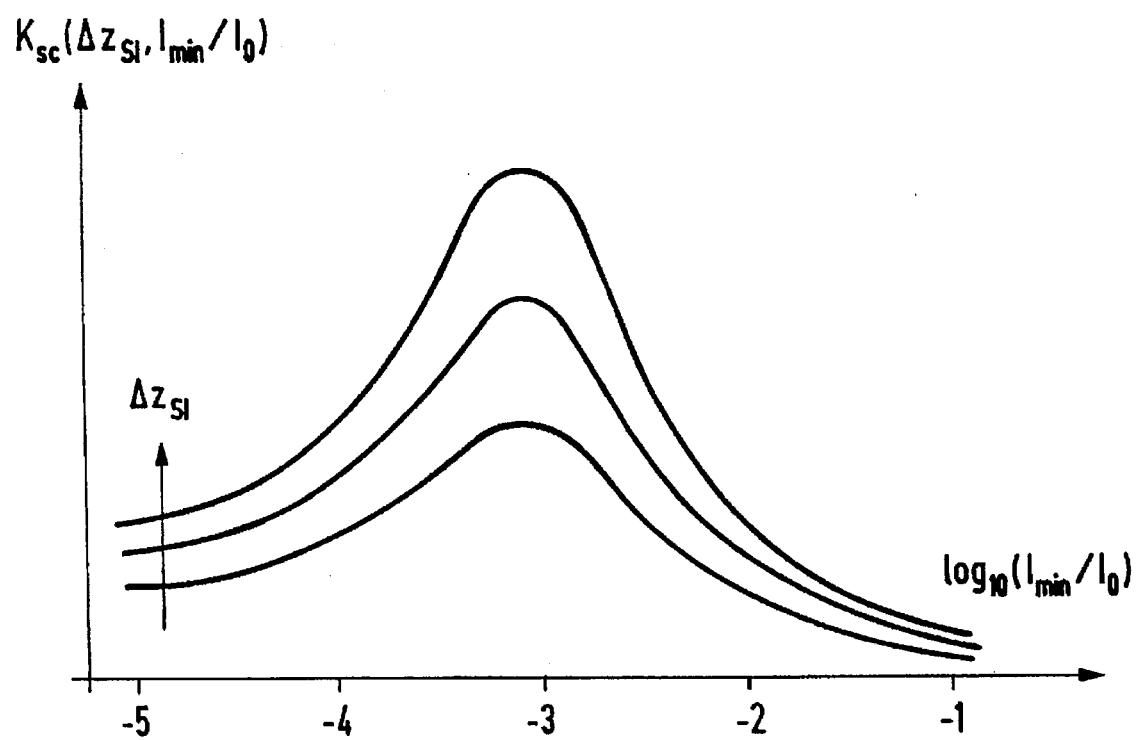

FIG. 3 shows the behavior in principle of $K_{sc}$ for a fourth-generation computed tomography (CT) system with one row of detectors. The tables must be experimentally determined for CTs of different construction through scattered radiation measurements or image quality optimizations, and can differ thoroughly from the curve shown in FIG. 3. The weighting function $f(\Delta_{S1})$ of the layer thickness thereby increases with layer thickness.

After the scatter intensities $I_{sc}(\delta,\gamma)$ have been determined for all channels in all projections with (9) to (12), they are subtracted from the measured data. After again taking the natural logarithms of the corrected with $I_0$ normalized intensities, the reconstruction of the corrected image is carried out in a known manner, but using the corrected intensities obtained as described above instead of the measured, uncorrected intensities.

The above considerations are based on the correction of focus fan projections in a fourth-generation CT with one detector row. In general, for a fourth-generation CT the images are reconstructed from detector fan projections. The correction can be carried out analogously in the detector fan data after modification of the parameters. In third-generation CTs, focus fan projections are basically surveyed. The usable detector collimators influence the correction parameters, which are to be correspondingly adapted.

Many reconstruction algorithms require data in parallel with beam geometry, obtained through a suitable interpolation from the fan data. The represented scattered radiation correction can then also be carried out in the parallel data. In addition, it is possible to apply the correction to intensity values normalized with the unattenuated primary intensity or to non-normalized intensity values.

The convolution of the forward scatter distribution with the distance function is carried out as multiplication of the discrete spectra in the frequency domain. The discrete Fourier transformation ensues with FFTs. Assuming that the scatter contributions do not vary erratically from projection to projection, it is sufficient to calculate the scatter contributions explicitly with the convolution for only a limited number of projections. The scatter intensities in the remaining projections can then be determined through a simple interpolation technique, such as, for example, a linear interpolation. The computing expense of the discrete convolution can be further reduced if the spectra of the distance function and the forward scatter distribution are sufficiently bandlimited. The FFTs can then be carried out in abbreviated form after a sub-sampling of the distance function and forward scatter distribution. A simple interpolation in the channel direction, such as again, e.g., a linear interpolation, finally supplies all necessary convolution values. Investigations have shown that with the measures described a savings in expense of up to 95% can be achieved.

The described corrections can also be used two-dimensionally in computer tomography systems with multiple-row detectors. In addition, the invention is also suited for two-dimensional correction in conventional x-ray equipment with surface-type detectors, i.e. with detectors constructed as a two-dimensional array of detector elements.

A parameterization of the correction can ensue by the application of a scale constant $K_{sc}$ to a table, which table depends on layer thickness and is subject-dependent. The dependence on layer thickness thereby proves to be a monotonously increasing function. The subject-dependence can be taken into account through the least intensity or maximum attenuation in the data set, or through the maximum subject extension. In addition, the correction can be carried out with data in focus fan or parallel geometry in third-generation CTs, or with data in focus fan, detector fan or parallel geometry in fourth-generation CTs. The scanners can access one or several detector rows.

Depending on the particular application, the numeric calculation of the subject-scattered radiation can be carried out with a one- or two-dimensional convolution of the forward scatter distribution with the distance function in a suitable coordinate system.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an x-ray examination apparatus having an x-ray source which emits x-rays with a primary radiation intensity and a detector array composed of a plurality of detector elements, each detector element generating an output signal representing an intensity distribution of all x-rays incident thereon, and a computer including calculating means for calculating an x-ray image of a subject disposed between said x-ray source and said detector array from said output signals, the improvement of said computer further including means for reducing artifacts arising in said x-ray image due to scattered radiation produced in said subject, comprising:

means for identifying a forward scatter intensity in each output signal, as a contribution to said intensity distribution, including means for windowing said measured intensity with a window function to obtain a windowed, measured intensity, for taking the natural logarithm of said intensity distribution, and for multiplying said natural logarithm of said intensity distribution with said windowed, measured intensity.

2. The improvement of claim 1 wherein said means for identifying a forward scatter intensity include means for normalizing said intensity distribution with respect to said primary radiation intensity to obtain a normalized intensity distribution, and wherein said means for taking the natural logarithm of said intensity distribution comprises means for taking the natural logarithm of said normalized intensity distribution, and wherein said means for multiplying said natural logarithm of said intensity distribution with said windowed, measured intensity comprise means for multiplying said natural logarithm of said normalized intensity distribution with said windowed, measured intensity.

3. In an x-ray examination apparatus having an x-ray source which emits x-rays with a primary radiation intensity and a detector array composed of a plurality of detector elements, each detector element generating an output signal representing an intensity distribution of all x-rays incident thereon, and a computer including calculating means for calculating an x-ray image of a subject disposed between said x-ray source and said detector array from said output signals, the improvement of said computer further including means for reducing artifacts arising in said x-ray image due to scattered radiation produced in said subject by identifying a distance function dependent on an extent of said subject in a direction of x-ray propagation comprising:

means for identifying a total scatter intensity means by convolving a forward scatter intensity with a distance function;

means for subtracting the total scatter intensity in each output signal from the respective output signal to obtain a plurality of corrected output signals; and wherein said calculating means comprise means for calculating said x-ray image from said corrected output signals.

4. The improvement of claim 3 further comprising means for weighting said total scatter intensity with a weighting function dependent on a distance of a center of gravity of a source of said scatter radiation from said detector array.

5. The improvement of claim 3 further comprising means for multiplying said forward scatter intensity by a scale constant obtained from a table of scale constants for respective layer thicknesses of said subject.

6. The improvement of claim 3 further comprising means for windowing said measured intensity with a window function to obtain a windowed, measured intensity, and wherein said means for identifying a total scatter intensity include means for normalizing said intensity distribution with respect to said primary radiation intensity to obtain a normalized intensity distribution, and means for taking the natural logarithm of said normalized intensity distribution, means for multiplying said natural logarithm of said normalized intensity distribution with said windowed, measured intensity to obtain a convolution result, and means for sampling said intensity distribution and said distance function before convolving said forward scatter intensity and said distance function, and interpolating said convolution result.

7. A method for operating an x-ray examination apparatus having an x-ray source which emits x-rays with a primary radiation intensity and a detector array composed of a plurality of detector elements, each detector element generating an output signal representing an intensity distribution of all x-rays incident thereon, and a computer including calculating means for calculating an x-ray image of a subject disposed between said x-ray source and said detector array from said output signals, said method reducing artifacts arising in said x-ray image due to scattered radiation produced in said subject, comprising the steps of:

identifying a forward scatter intensity in each output signal, by windowing said measured intensity with a window function to obtain a windowed, measured intensity, taking the natural logarithm of said intensity distribution, and multiplying said natural logarithm of said intensity distribution with said windowed, measured intensity.

8. The method of claim 7 wherein the step of identifying a forward scatter intensity includes normalizing said intensity distribution with respect to said primary radiation intensity to obtain a normalized intensity distribution, and wherein the steps of taking the natural logarithm of said intensity distribution comprises taking the natural logarithm of said normalized intensity distribution, and wherein the steps of multiplying said natural logarithm of said intensity distribution with said windowed, measured intensity comprises multiplying said natural logarithm of said normalized intensity distribution with said windowed, measured intensity.

9. A method for operating an x-ray examination apparatus having an x-ray source which emits x-rays with a primary radiation intensity and a detector array composed of a plurality of detector elements, each detector element generating an output signal representing an intensity distribution of all x-rays incident thereon, and a computer including calculating means for calculating an x-ray image of a subject disposed between said x-ray source and said detector array from said output signals, said method reducing artifacts arising in said x-ray image due to scattered radiation produced in said subject by identifying a distance function dependent on an extent of said subject in a direction of x-ray propagation comprising the steps of:

identifying a total scatter intensity by convolving a forward scatter intensity with a distance function;

subtracting the forward scatter intensity in each output signal from the respective output signal to obtain a plurality of corrected output signals; and calculating said x-ray image from said corrected output signals.

10. The method of claim 9 further comprising the additional step of weighting said total scatter intensity with a weighting function dependent on a distance of a center of gravity of a source of said scatter radiation from said detector array.

11. The method of claim 9 comprising the additional step of multiplying said total scatter intensity by a scale constant obtained from a table of scale constants for respective layer thicknesses of said subject.

12. The method of claim 9 comprising the further step of windowing said measured intensity with a window function to obtain a windowed, measured intensity, and wherein the step of identifying a total scatter intensity includes identifying said forward scatter intensity by normalizing said intensity distribution with respect to said primary radiation intensity to obtain a normalized intensity distribution, taking the natural logarithm of said normalized intensity distribution, multiplying said natural logarithm of said normalized intensity distribution with said windowed, measured intensity to obtain a convolution result, and sampling said intensity distribution and said distance function before convolving said forward scatter intensity and said distance function, and interpolating said convolution result.

* * * * *